United States Patent
Fujii et al.

(10) Patent No.: US 7,754,205 B2
(45) Date of Patent: Jul. 13, 2010

(54) COMPOSITION FOR TRANSMUCOSAL ADMINISTRATION CONTAINING CONENZYME Q AS THE ACTIVE INGREDIENT

(75) Inventors: Kenji Fujii, Kobe (JP); Taizo Kawabe, Himeiji (JP); Kazunori Hosoe, Takasago (JP); Takayoshi Hidaka, Kobe (JP)

(73) Assignee: Kaneka Corporation, Osaka (JP)

( * ) Notice: Subject to any disclaimer, the term of this patent is extended or adjusted under 35 U.S.C. 154(b) by 1432 days.

(21) Appl. No.: 10/476,208

(22) PCT Filed: May 8, 2002

(86) PCT No.: PCT/JP02/04476

§ 371 (c)(1), (2), (4) Date: Oct. 28, 2003

(87) PCT Pub. No.: WO02/092067

PCT Pub. Date: Nov. 21, 2002

(65) Prior Publication Data

US 2004/0115181 A1    Jun. 17, 2004

(30) Foreign Application Priority Data

May 10, 2001    (JP)    ............................. 2001-139605

(51) Int. Cl.
*A61K 38/43*    (2006.01)
(52) U.S. Cl. ...................... 424/94.1; 424/433; 424/430; 424/49; 424/427; 424/434; 424/436; 424/437; 424/439; 514/882
(58) Field of Classification Search .............. 424/434, 424/49, 94.1, 427, 430, 433, 436, 437, 439; 524/358; 252/393; 514/882
See application file for complete search history.

(56) References Cited

U.S. PATENT DOCUMENTS

| 4,599,232 | A | * | 7/1986 | Bertelli | ...................... 424/94.1 |
| 5,378,461 | A | * | 1/1995 | Neigut | ...................... 424/94.1 |
| 6,048,886 | A | * | 4/2000 | Neigut | ...................... 514/412 |
| 6,087,351 | A |   | 7/2000 | Nyce | |
| 6,184,255 | B1 | * | 2/2001 | Mae et al. | .................... 514/720 |
| 6,228,891 | B1 |   | 5/2001 | Enzmann et al. | |
| 6,686,485 | B2 | * | 2/2004 | West | .......................... 552/307 |
| 6,814,972 | B2 | * | 11/2004 | Cavazza | ..................... 424/400 |
| 2002/0032160 | A1 | * | 3/2002 | Nyce | ............................ 514/26 |
| 2004/0034107 | A1 |   | 2/2004 | Enzmann et al. | |
| 2004/0126367 | A1 | * | 7/2004 | Fujii et al. | ................. 424/94.1 |
| 2006/0073131 | A1 | * | 4/2006 | Fujii et al. | ................. 424/94.1 |

FOREIGN PATENT DOCUMENTS

| CA | 2362575 A1 | 8/2000 |
| DE | 19802050 A | 7/1999 |
| DE | 19905880 A | 8/2000 |
| DE | 19905879 A1 | 2/2004 |
| WO | WO 99/22703 A | 5/1999 |
| WO | 00/33802 A1 | 6/2000 |
| WO | 00/47185 A1 | 8/2000 |
| WO | 01/52822 A1 | 7/2001 |

OTHER PUBLICATIONS

Frei, B., Ubiquinol-10 is an effective lipid-soluble antioxidant at physiological concentrations, University of California, Medical Sciences, vol. 87, pp. 4879-4883, Jun. 1990.*

Yamamoto, Y., Plasma Ratio of Ubiquinol and Ubiquinone as a Marker of Oxidative Stress, Elsevier, Molec. Aspects Med., vol. 18, pp. s79-s84.*

Staoshi Shizukuishi, et al.; "Effect of Coenzyme $Q_{10}$ on Experimental Periodontitis in Dogs"; Biomedical Research; vol. 4; No. 1; pp. 33-40; 1983.

* cited by examiner

*Primary Examiner*—Johann R Richter
*Assistant Examiner*—Danielle Sullivan
(74) *Attorney, Agent, or Firm*—Sughrue Mion, PLLC

(57) ABSTRACT

The present invention relates to the supply of coenzyme Q which is highly useful in maintaining human health, and provides a method and preparations whereby coenzyme Q can be efficiently supplied to patients having difficulties in oral administration, aged having swallowing difficulties and patients with diseases caused by topical disorders. It is found that the coenzyme Q concentration in the blood or topical mucosae can be elevated by using a composition for transmucosal administration containing oxidized coenzyme Q and/or reduced coenzyme Q as the active ingredient, wherein the total content of the oxidized coenzyme Q and the reduced coenzyme Q amounts to 0.0001 to 99% by weight of the whole composition.

13 Claims, No Drawings

COMPOSITION FOR TRANSMUCOSAL ADMINISTRATION CONTAINING CONENZYME Q AS THE ACTIVE INGREDIENT

TECHNICAL FIELD

The present invention relates to a composition for transmucosal administration containing coenzyme Q as an active ingredient.

BACKGROUND ART

Coenzyme Q is an essential component which is distributed in a wide variety of living organisms ranging from bacteria to mammals. It is known that coenzyme Q undergoes oxidation/reduction cycles in living organisms and functions as an electron carrier in an electron transport system, and reduced coenzyme Q is an antioxidant. It is also known that in many animals including humans, fishes, and birds, coenzyme Q is mainly composed of coenzyme $Q_{10}$ having 10 repeat structures in its side chain, and about 40% to 90% of coenzyme Q present in living organisms is generally in its reduced form. Since coenzyme Q can be synthesized in living organisms, coenzyme Q does not belong to the vitamin group, but it is thought to be substantially the same as vitamins. Also, the human ability of biosynthesis of coenzyme $Q_{10}$ decreases with aging to decrease the coenzyme $Q_{10}$ content in living organisms, and thus the need for supplying coenzyme $Q_{10}$ in some form is demanded.

In coenzyme $Q_{10}$ oxidized coenzyme $Q_{10}$ is used as an agent for a congestive heart failure in medical applications. In addition to medical applications, oxidized coenzyme $Q_{10}$ is used as a nutritional supplement or nutritional adjuvant like vitamins, or used for effectively treating an allergic disease or increasing athletic ability. Therefore, the effectiveness of oxidized coenzyme $Q_{10}$ has been reported in a wide variety of fields. Furthermore, the effectiveness for brain diseases such as dementia, and the like has been reported, and it can thus be expected that oxidized coenzyme $Q_{10}$ has high effectiveness for elderly persons.

In this way, coenzyme $Q_{10}$ has high usefulness, and no toxicity is observed in a safety test using animals, in which coenzyme $Q_{10}$ is continuously administered to rats for 52 weeks with a high dose of 1.2 g/kg/day. Therefore, the coenzyme $Q_{10}$ is a compound proved to have high safety (J. Agric. Food Chem., 1999, Vol. 47, P3756-3763). However, coenzyme $Q_{10}$ is only actually used as a skin agent other than oral administration, and thus has difficulties in practical administration to a patient with a serious disease, an elderly person or a young child who cannot easily orally intake coenzyme $Q_{10}$. Furthermore, in a topical site such as the intestinal canal, the nose, or the ears, which are easily affected by an allergic disease, a sufficient concentration of coenzyme Q cannot be obtained by oral administration. Therefore, in fact, coenzyme Q cannot be effectively utilized.

SUMMARY OF THE INVENTION

An object of the present invention is to provide a preparation which contains coenzyme Q as an active ingredient, and which can be easily used for a patient or elderly person having difficulties in oral administration, or which can effectively supply coenzyme Q to a topical site where a sufficient concentration of coenzyme Q cannot be easily obtained.

As a result of studies for solving the above problem, the inventors found that coenzyme Q can be absorbed into the body through mucosal absorption. It was also found that by using a composition containing reduced coenzyme Q, a high blood concentration of coenzyme Q can be obtained by a preparation of coenzyme Q, as compared with a composition containing only oxidized coenzyme Q. It was further found that coenzyme Q can be effectively transferred to a topical site through mucosal absorption.

A composition for transmucosal administration of the present invention comprises, as an active ingredient, oxidized coenzyme Q represented by formula (1) and/or reduced coenzyme Q represented for formula (2):

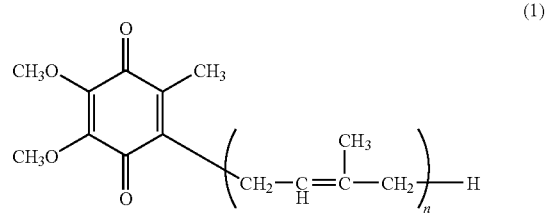

(wherein n represents an integer of 1 to 12)

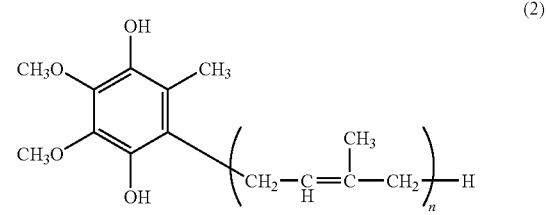

(wherein n represents an integer of 1 to 12),
wherein the total content of oxidized coenzyme Q and reduced coenzyme Q is 0.0001 to 99% by weight of the whole of the composition. The composition may be applied to humans or animals. Examples of animals include pet animals such as dogs, cats, and the like, race horses, domestic animals such as cows, horses, pigs, rabbits, rats, mice, and the like, birds, and the like.

In the present invention, a "composition for transmucosal administration" means a composition produced in a form to be absorbed into the body through the mucosae. In the present invention, "the mucosae" includes the intestine, the nasal mucosa, the oral mucosa, the otic mucosa, the vaginal mucosa, and the like.

The present invention provides the composition for transmucosal administration applied to humans or animals, and thus the present invention also provides a method for transferring coenzyme Q into the body. Furthermore, the present invention provides the composition for transmucosal administration applied to the mucosae of humans or animals having diseases, and thus provides a method for treating diseases. As conditions for applications, generally known conditions can be used according to the form of the composition used. For example, in the case of a suppository, a suppository containing coenzyme Q is preferably used once a day. In this case, the content of coenzyme Q is preferably 30 mg to 100 mg, and more preferably 50 mg to 100 mg. In the case of eye drops or nose drops, eye drops or nose drops containing coenzyme Q are preferably 2 or 3 times a day. In this case, the content of coenzyme Q is preferably 0.01% by weight to 10% by weight, and more preferably 0.1% by weight to 3% by weight.

DETAILED DISCLOSURE OF INVENTION

The present invention will be described in detail below.

A compound represented by the above formula (1) is oxidized coenzyme Q, and a compound represented by the above formula (2) is reduced coenzyme Q.

The method for obtaining oxidized coenzyme Q and reduced coenzyme Q is not limited, and for example, a method comprising obtaining coenzyme Q by a conventional known process such as synthesis, fermentation, extraction from a natural source, or the like, and then concentrating each fraction from a chromatography eluate can be used. In order to obtain reduced coenzyme Q, if required, a general reducing agent such as sodium borohydride, sodium dithionite (sodium hydrosulfite), or the like may be added to the coenzyme Q, for reducing oxidized coenzyme Q contained in coenzyme Q to reduced coenzyme Q by a conventional process, and then the obtained reduced coenzyme Q may be concentrated by chromatography. Reduced coenzyme Q can also be obtained by applying a reducing agent to existing oxidized coenzyme Q.

As the oxidized coenzyme Q and reduced coenzyme Q used in the present invention, as shown in formulae (1) and (2), a coenzyme having 1 to 12 side chain repeat units (n in each formula) can be used. Particularly, a coenzyme having 10 side chain repeat units, i.e., oxidized coenzyme $Q_{10}$ and reduced coenzyme $Q_{10}$, can be preferably used.

Although the content of coenzyme Q in the composition of the present invention is appropriately determined by the application and dosage form, the lower limit of the total content (the content of oxidized coenzyme Q of the whole of the composition when the composition contains only oxidized coenzyme Q, and the content of reduced coenzyme Q of the whole of the composition when the composition contains only reduced coenzyme Q) of the oxidized coenzyme Q and the reduced coenzyme Q is 0.0001% by weight of the whole of the composition, and the upper limit is 99% by weight. Preferably, the lower limit is 0.005% by weight, and the upper limit is 50% by weight. More preferably, the lower limit is 0.01% by weight, and the upper limit is 30% by weight.

When the composition of the present invention contains both oxidized coenzyme Q and reduced coenzyme Q, the content of reduced coenzyme Q of the whole of oxidized coenzyme Q and reduced coenzyme Q preferably exceeds 20% by weight, and is more preferably 40% by weight or more. The upper limit of the content may be 100% by weight or less, preferably less than 100% by weight, and more preferably 98% by weight or less.

The composition for transmucosal administration of the present invention can be prepared in formulations such as a suppository, a vaginal suppository, nose drops, ear drops, an oral mucosal applicator, toothpaste, a troche, a drop, an electuary, an oral solubilizer, and the like according to the administration route. Each of these formulations can be produced by a conventional known formulation method using formulation additives generally used for the formulation.

In the case of a suppository formulation, examples of formulation additives include semi-synthetic hardened oils such as Isocacao (produced by Kao Corporation), Witepsol (produced by Huls Corp.), Suppocire (Gattefosse Corp.), Pharmasol (produced by NOF Corporation), Massa Estarinum (produced by Huls Corp.), Novata (produced by Henkel Corp.), a SB base (produced by Taiyo Oil K. K.), and the like; natural fats and oils such as cacao butter, palm butter, palm seed oil, palm oil, fractional coconut oil, lard, and the like; waxes such as lanoline, reduced lanoline, and the like; hydrocarbons such as vaseline, squalene, squalane, liquid paraffin, and the like; higher alcohols such as lauryl alcohol, cetanol, stearyl alcohol, and the like; fatty acid esters such as butyl stearate, dilauryl malonate, and the like; glycerin medium-chain carboxylic acid esters such as triolein, tristealin, and the like; glycerin-substituted carboxylic acid esters such as glycerin acetoacetic ester, and the like; polyethylene glycol and derivatives thereof such as macrogol, acetomacrogol, and the like.

In the case of nose drops formulation, examples of formulation additives include physiological saline; buffers such as a lactate buffer, an acetate buffer, a phosphate buffer, and the like; bactericidal and antiseptic agents such as paraoxybenzoic acid esters, propylene glycol, benzetonium chloride, benzalkonium chloride, sorbic acid or its salts, chlorobutanol, and the like; thickening agents such as polyvinyl alcohol, polyvinylpyrrolidone, dextran, alginic acid metal salts, saccharose, gelatin, methyl cellulose, hyaluronic acid metal salts, and the like; bases for powder administration such as crystalline cellulose, α-cellulose, sodium crosslinked-carboxymethyl cellulose, hydroxypropyl cellulose, β-cyclodextrin, dimethyl-β-cyclodextrin, lactose, and the like.

The composition of the present invention may further contain an absorption promoter suitable for each of the dosage forms and purposes.

The composition for transmucosal administration of the present invention can be used for medical products. In this case, examples of diseases to be treated include hemorrhoid, idiopathic ulcerative colitis, a Crohn's disease, a heart failure, cerebropathy, cerebral infarction, diabetes, diabetic retinopathy, cardiac infarction, allergic rhinitis, pollinosis, conjunctivitis, gingivitis, alveolar pyorrhea, and the like. In this case, the composition may further contain medical components other than coenzyme Q.

In the present invention, a suppository may contain a drug generally used for an intestinal disease such as hemorrhoid, idiopathic ulcerative colitis, a Crohn's disease, or the like; or a substance used for the whole body, such as an antipyretic analgesic, a nutritional adjuvant, or the like.

In the present invention, nose drops may contain a drug generally used for allergic rhinitis or pollinosis.

In the present invention, toothpaste may contain a drug generally used for gingivitis or alveolar pyorrhea.

The composition for transmucosal administration of the present invention can also be used for alimentation. In this case, the composition may further contain a nutritional adjuvant. Examples of the nutritional adjuvant include vitamins, crude drug extracts, herb extracts, polyphenols, propolis, and the like.

BEST MODE FOR CARRYING OUT THE INVENTION

Although the present invention will be described in further detail below with reference to examples and formulation examples, the present invention is not limited to these examples.

Example 1

(1) Preparation of Specimen Sample 1

1 g of oxidized coenzyme $Q_{10}$ was melted on a water bath at 50° C., and then macrogol 1000 (PEG 1000) was added to form 10 ml of mixture. The resultant mixture was homogeneously melt-mixed at 50° C., and then solidified at room temperature to form a cylindrical suppository having a diameter of about 5 mm.

(2) Preparation of Specimen Sample 2

1 g of reduced coenzyme $Q_{10}$ (containing 5% of oxidized coenzyme $Q_{10}$) was melted on a water bath at 50° C., and then macrogol 1000 (PEG 1000) melted by the same method was added to form 10 ml of mixture. The resultant mixture was homogenously melt-mixed at 50° C., and then solidified at room temperature to form a suppository. The content of reduced coenzyme $Q_{10}$ in the suppository was 95% of the whole of the coenzyme $Q_{10}$ and oxidation was not observed during preparation.

(3) Test of Transmucosal Absorption

Each of specimen samples 1 and 2 was used as a test sample. The test was performed by using male Wistar rats (body weight 250 to 300 g) fasted for one night. Test specimen 1 or 2 was inserted into the intestinum rectum of each rat with a dose of 1 g/kg. After insertion, the blood was collected with time to determine the amount of coenzyme $Q_{10}$ in the blood plasma. The amount of the coenzyme $Q_{10}$ in the blood plasma is shown in Table 1. Each of values is average±standard deviation with n=10.

TABLE 1

| | Amount of coenzyme $Q_{10}$ in blood plasma (ng/ml) | |
|---|---|---|
| Time | Suppository containing oxidized coenzyme $Q_{10}$ | Suppository containing reduced coenzyme $Q_{10}$ |
| 0 | 12.88 ± 1.94 (100) | 13.79 ± 1.34 (100) |
| 1 | 11.67 ± 2.33 (91) | 14.86 ± 1.89 (108) |
| 2 | 18.51 ± 4.56 (144*) | 17.68 ± 3.55 (128) |
| 4 | 15.96 ± 3.61 (124) | 21.55 ± 4.61 (156*) |
| 8 | 15.63 ± 3.30 (121) | 37.61 ± 4.88 (272***) |
| 12 | 14.75 ± 2.99 (115) | 46.11 ± 6.09 (334***) |
| 24 | 11.37 ± 1.87 (88) | 28.64 ± 5.50 (207***) |

*$p < 0.05$,
**$p < 0.01$,
***$p < 0.001$ Student t-test

As described above, it was found that the amount of coenzyme $Q_{10}$ in the blood plasma can be increased by transmucosal administration of coenzyme $Q_{10}$ used as a suppository. This result indicates that coenzyme $Q_{10}$ which can be only orally administered because of its insolubility can be supplied by transmucosal administration even when oral administration is difficult. It is further surprising that the amount of coenzyme $Q_{10}$ in the blood plasma can be more increased by a suppository comprising coenzyme $Q_{10}$ containing 95% of reduced coenzyme $Q_{10}$, as compared with coenzyme $Q_{10}$ containing 100% of oxidized coenzyme $Q_{10}$. It is thus found that the suppository comprising coenzyme $Q_{10}$ containing 95% of reduced coenzyme $Q_{10}$ is excellent in supplying coenzyme $Q_{10}$ to living organisms.

Example 2

Test of Mucosal Transition Ability

Suppositories containing oxidized and reduced coenzyme $Q_{10}$, respectively, were prepared by the same method as in Example 1. The transition ability of coenzyme $Q_{10}$ to the colic mucosa of a rat was evaluated by using each suppository. In the test, specimen sample 1 or 2 was inserted into the colon of each of male Wistar rats with a dosage of 1 g/kg in the same manner as in Example 1. After insertion, the colon was collected from each rat with time and then sufficiently washed to determine the amount of coenzyme $Q_{10}$ in the colic tissue by high performance liquid chromatography (HPLC). The amount of coenzyme $Q_{10}$ in the colic tissue is shown in Table 2. Each of values is average±standard deviation with n=5.

TABLE 2

| | Amount of coenzyme $Q_{10}$ in colon (μg/g) | |
|---|---|---|
| Time | Suppository containing oxidized coenzyme $Q_{10}$ | Suppository containing reduced coenzyme $Q_{10}$ |
| 0 | 0.88 ± 0.21 (100) | 0.73 ± 0.15 (100) |
| 2 | 1.22 ± 0.31 (138) | 1.78 ± 0.56 (243*) |
| 4 | 1.41 ± 0.48 (160) | 2.37 ± 0.62 (325**) |
| 8 | 1.29 ± 0.32 (147) | 2.19 ± 0.53 (300**) |
| 24 | 1.07 ± 0.31 (122) | 1.64 ± 0.41 (224*) |

*$p < 0.05$,
**$p < 0.01$ Student t-test

As described above, it was found that the amount of coenzyme $Q_{10}$ in the colic mucosa can be increased by transmucosal administration of coenzyme $Q_{10}$ used as a suppository. This result indicates that coenzyme $Q_{10}$ can be effectively supplied to the mucosa. It is further surprising that the amount of coenzyme $Q_{10}$ in the mucosa can be more increased by a suppository comprising coenzyme $Q_{10}$ containing 95% of reduced coenzyme $Q_{10}$, as compared with coenzyme $Q_{10}$ containing 100% of oxidized coenzyme $Q_{10}$. It is thus found that the suppository comprising coenzyme $Q_{10}$ containing 95% of reduced coenzyme $Q_{10}$ is excellent in supplying coenzyme $Q_{10}$ to the mucosae.

Preparation Example 1

Suppository

| | |
|---|---|
| Coenzyme $Q_{10}$ | 1.0 g |
| Macrogol | 100 g in total |

However, coenzyme $Q_{10}$ has a reduced form/oxidized form ratio of 98:2.

Preparation Example 2

Eye Drops

| | |
|---|---|
| Coenzyme $Q_{10}$ | 0.1 g |
| Glycerin | 1.0 g |
| Propylene glycol | 1.0 g |
| Polysolvate 80 | 1.5 g |
| Sodium dihydrogen phosphate | 0.1 g |
| Benzalkonium chloride | 0.005 g |
| Distilled water | 100 mL in total |

However, coenzyme $Q_{10}$ has a reduced form/oxidized form ratio of 98:2.

INDUSTRIAL APPLICABILITY

The composition of the present invention has the above-described constitution, and is thus excellent in supplying coenzyme Q to the whole body by a method other than oral administration, and in accumulating coenzyme Q in the topical mucosae. Therefore, the composition exhibits excellent effects on health care of aged persons or patients with serious diseases, and on diseases occurring in the topical mucosae, such as an allergic disease and the like.

The invention claimed is:

1. A method for transferring coenzyme Q into a living organism, comprising applying a composition comprising, as an active ingredient, reduced coenzyme Q represented by formula (2), or, a mixture of oxidized coenzyme Q represented by formula (1) and reduced coenzyme Q represented by formula (2) to a mucosa which is the intestine, the nasal mucosa, the otic mucosa or the vaginal mucosa:

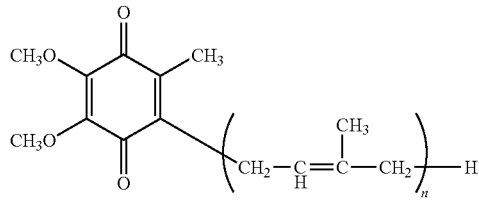
(1)

(wherein n represents an integer of 1 to 12)

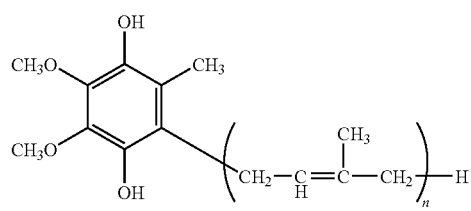
(2)

(wherein n represents an integer of 1 to 12), wherein the total content of oxidized coenzyme Q and reduced coenzyme Q is 0.0001 to 99% by weight of the whole of the composition and the proportion of reduced coenzyme Q relative to the total amount of oxidized coenzyme Q and reduced coenzyme Q exceeds 20 wt %.

2. A method according to claim 1, wherein the oxidized coenzyme Q represented by formula (1) is oxidized coenzyme $Q_{10}$, and the reduced coenzyme Q represented by formula (2) is reduced coenzyme $Q_{10}$.

3. A method according to claim 1, wherein the proportion of reduced coenzyme Q relative to the total amount of oxidized coenzyme Q and reduced coenzyme Q exceeds 20 wt %.

4. A method for increasing the amount of coenzyme Q in a mucosa,
comprising applying a composition comprising, as an active ingredient, reduced coenzyme Q represented by formula (2), or, a mixture of oxidized coenzyme Q represented by formula (1) and reduced coenzyme Q represented for formula (2) to the mucosa which is the intestine, the nasal mucosa, the otic mucosa or the vaginal mucosa:

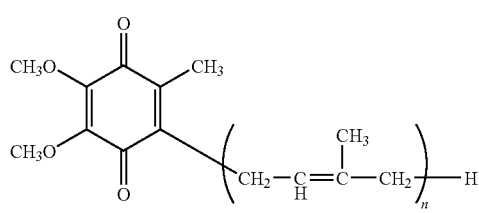
(1)

(wherein n represents an integer of 1 to 12)

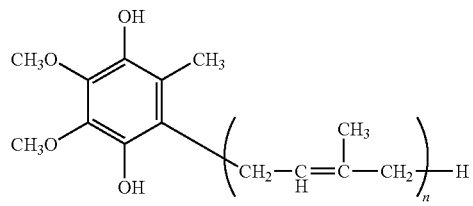
(2)

(wherein n represents an integer of 1 to 12), wherein the total content of oxidized coenzyme Q and reduced coenzyme Q is 0.0001 to 99% by weight of the whole of the composition and the proportion of reduced coenzyme Q relative to the total amount of oxidized coenzyme Q and reduced coenzyme Q exceeds 20 wt %.

5. A method according to claim 4, wherein the oxidized coenzyme Q represented by formula (1) is oxidized coenzyme $Q_{10}$, and the reduced coenzyme Q represented by formula (2) is reduced coenzyme $Q_{10}$.

6. A method for treating a disease selected from the group consisting of hemorrhoid, an intestinal disease, allergic rhinitis, pollinosis and conjunctivitis,
comprising applying to a subject having the disease a composition comprising, as an active ingredient, reduced coenzyme Q represented by formula (2), or, a mixture of oxidized coenzyme Q represented by formula (1) and reduced coenzyme Q represented by formula (2) to a mucosa:

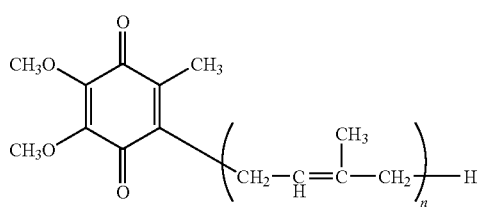
(1)

(wherein n represents an integer of 1 to 12)

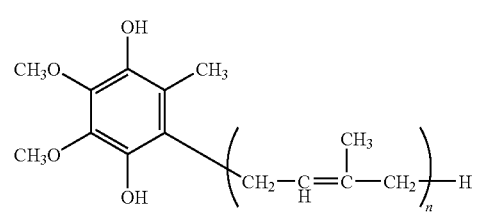
(2)

(wherein n represents an integer of 1 to 12), wherein the total content of oxidized coenzyme Q and reduced coenzyme Q is 0.0001 to 99% by weight of the whole of the composition and the proportion of reduced coenzyme Q relative to the total amount of oxidized coenzyme Q and reduced coenzyme Q exceeds 20 wt %.

7. A method according to claim 6, wherein the oxidized coenzyme Q represented by formula (1) is oxidized coenzyme $Q_{10}$, and the reduced coenzyme Q represented by formula (2) is reduced coenzyme $Q_{10}$.

8. A method according to claim 6, wherein the mucosa is the intestine, the nasal mucosa, the otic mucosa or the vaginal mucosa.

9. A formulation for transmucosal administration for treating a disease selected from the group consisting of hemorrhoid, an intestinal disease, allergic rhinitis, pollinosis and conjunctivitis comprising, as an active ingredient, reduced coenzyme Q represented by formula (2), or, a mixture of oxidized coenzyme Q represented by formula (1) and reduced coenzyme Q represented for formula (2):

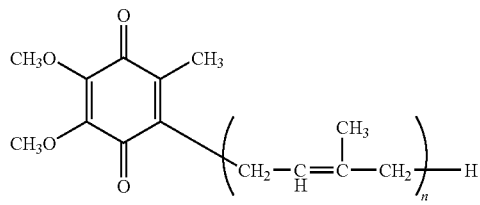

(1)

(wherein n represents an integer of 1 to 12)

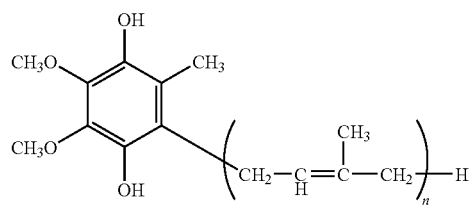

(2)

(wherein n represents an integer of 1 to 12), wherein the formulation is selected from the group consisting of a suppository, nose drops, ear drops, eye drops, an oral mucosal applicator, a troche, an electuary, a vaginal suppository and a toothpaste, and the total content of oxidized coenzyme Q and reduced coenzyme Q is 0.0001 to 99% by weight of the whole of the composition and the proportion of reduced coenzyme 0 relative to the total amount of oxidized coenzyme Q and reduced coenzyme Q exceeds 20 wt %.

10. A formulation according to claim 9, wherein the oxidized coenzyme Q represented by formula (1) is oxidized coenzyme $Q_{10}$, and the reduced coenzyme Q represented by formula (2) is reduced coenzyme $Q_{10}$.

11. A formulation according to claim 9, further comprising a medicinal ingredient other than oxidized coenzyme Q represented by formula (1) and reduced coenzyme Q represented by formula (2).

12. A formulation according to claim 9, which is a suppository, and wherein the content of coenzyme Q is not less than 30 mg and not more than 100 mg.

13. A method according to claim 9, which is eye drops or nose drops, and wherein the content of coenzyme Q is 0.01% to 10% by weight.

* * * * *

UNITED STATES PATENT AND TRADEMARK OFFICE
CERTIFICATE OF CORRECTION

PATENT NO. : 7,754,205 B2  
APPLICATION NO. : 10/476208  
DATED : July 13, 2010  
INVENTOR(S) : Kenji Fujii et al.

Page 1 of 1

It is certified that error appears in the above-identified patent and that said Letters Patent is hereby corrected as shown below:

In the Claims:

Claim 9,
Column 10, Line 8: Delete "coenzyme 0" and insert -- coenzyme Q --

Signed and Sealed this
Fourteenth Day of May, 2013

Teresa Stanek Rea
*Acting Director of the United States Patent and Trademark Office*